US00PP12826P2

(12) United States Plant Patent
Snow

(10) Patent No.: US PP12,826 P2
(45) Date of Patent: Aug. 6, 2002

(54) BEGONIA PLANT NAMED '77KK BLUSH PINK'

(75) Inventor: Andrew B. Snow, Aptos, CA (US)

(73) Assignee: Golden State Bulb Growers, Moss Landing, CA (US)

( * ) Notice: Subject to any disclaimer, the term of this patent is extended or adjusted under 35 U.S.C. 154(b) by 0 days.

(21) Appl. No.: 09/489,008

(22) Filed: Jan. 21, 2000

(51) Int. Cl.[7] ..... A01H 5/00
(52) U.S. Cl. ..... Plt./348
(58) Field of Search ..... Plt./348, 344, 345

*Primary Examiner*—Bruce R. Campell
*Assistant Examiner*—W C Baker

(74) *Attorney, Agent, or Firm*—Foley & Lardner

(57) ABSTRACT

A new and distinct cultivar of Begonia plant named '77KK Blush Pink' characterized by having a definite and distinct flower fragrance that can be described as sweet and lingering but subtle and not overpowering. It is often compared to the scent of a fragrant rose bloom. The fragrance is most pronounced when the temperature is between 65° and 80° F. The cultivar has a subtle blush-color flower which is primarily white with a pink cast. The male flowers are fully double and do not produce pollen or male reproductive parts under normal growing conditions. '77KK Blush Pink' has a full and semi-pendulous plant habit with numerous flower shoots (4–6 or more). Each flowering shoot will produce anywhere from 4–6 peduncles with 1 or 2 male flowers on each during the growing season.

2 Drawing Sheets

BACKGROUND OF THE INVENTION

The present invention relates to a new and distinctive cultivar of Begonia plant, botanically known as *Begonia tuberhybrida* (Pendula-type), and known by the cultivar name '77KK Blush Pink'.

The new cultivar is a product of a planned breeding program and was originated from a hybridization made during such a program in Watsonville, Calif. in 1992. The female or seed parent was a proprietary Begonia selection designated 77HT-3065. The male or pollen parent was a proprietary Begonia selection designated 77HS-3068. '77KK Blush Pink' was discovered and selected within the progeny of the stated cross by the inventor, Andrew B. Snow, in a controlled environment in Watsonville, Calif. in 1993.

The first act of asexual reproduction of '77KK Blush Pink' was accomplished by leaf and stem cuttings in 1995 in a controlled environment in Moss Landing, Calif. by Andrew B. Snow. Horticultural examination of selected units has demonstrated that the combination of characteristics as herein disclosed for '77KK Blush Pink' are firmly fixed and are retained through successive generations of asexual reproduction.

BRIEF DESCRIPTION OF THE INVENTION

The following characteristics distinguish the new cultivar from both its parents and other Begonia cultivars commercially known and used in the floriculture industry:

1. A definite and distinct flower fragrance that can be described as sweet and lingering but subtle and not overpowering. It is often compared to the scent of a fragrant rose bloom. The fragrance is most pronounced when the temperature is between 65° and 80° F.;
2. A subtle blush-color flower which is primarily white with a pink cast;

3. Male flowers which are fully double and do not produce pollen or male reproductive parts under normal growing conditions; and
4. Full and semi-pendulous plant habit with numerous flower shoots (4–6 or more). Each flowering shoot will produce anywhere from 4–6 peduncles with 1 or 2 male flowers on each during the growing season.

'77KK Blush Pink' has not been observed under all possible environmental conditions. The phenotype of the new cultivar may vary significantly with variations in environment such as temperature, light intensity, and daylength, without any change in genotype.

Of the many commercial cultivars known to the present inventor, there is no known Begonia cultivar with which the new cultivar can be meaningfully compared. The color variance and gradation is unique, as is the distinct fragrance.

BRIEF DESCRIPTION OF THE DRAWINGS

The accompanying color photographic illustrations were taken on Aug. 20, 1999, and show typical flower and foliage characteristics of '77KK Blush Pink' when grown in a 10-inch plastic pot, with colors being as true as possible with illustrations of this type.

The first drawing is a side elevational view of '77KK Blush Pink'.

The second drawing is a top view of the claimed cultivar showing characteristics of the upper and lower surfaces of the flower and foliage.

DETAILED BOTANICAL DESCRIPTION

The following observations, measurements, and values describe a 3 year old tuber of '77KK Blush Pink' as grown in Watsonville, Calif. under conditions which approximate those generally used in commercial practice. The plant is grown in a greenhouse with ambient temperatures of 60–75° F. The greenhouse is provided with a 50% shade cover that limits the light to under 2000 foot-candles. '77KK Blush Pink' is grown in a soiless mix and fed with a regular, complete fertilizer such as 20-10-20 at a rate of 200 ppm N, once every week.

Color references are made to The Royal Horticultural Society (R.H.S.) Colour Chart except where general terms of ordinary dictionary significance are used.

Classification:

*Botanical.*—A hybrid of the genus *Begonia tuberhybrida* (Pendula-type).

*Commercial.*—Begonia cv. 77KL Sunrise.

Parentage:

*Male parent.*—Begonia cultivar designated 77HS-3068.

*Female parent.*—Begonia cultivar designated 77HT-3065.

Propagation:

*Type cutting.*—Leaf and stem cuttings.

*Time to root.*—Approximately 24 to 30 days at 21° C. (summer) and 32 to 38 days at 21° C. (winter).

*Rooting habit/description.*—Abundant, fibrous and dendritic.

*Time for shoot development.*—Slow, 10 to 14 weeks in summer and up to 16 weeks in winter.

Plant:

*Form.*—Low mounding, semi-pendulous and herbaceous.

*Growth habit.*—Slow, uniform growth with numerous shoots and moderate branching habit at full growth. The plant is well rounded with a height of about 10 to 15 inches, excluding the container, with up to 20-inch pendulous shoots. The width is approximately 24 inches, stem color is red, RHS 45A, where the stem receives direct light and yellow-green, RHS 154D, where the stem receives indirect light.

*Vigor.*—'77KK Blush Pink' makes a full vigorous plant approximately 12 weeks after planting a tuber, which has been given a sufficient dormant period, under greenhouse growing conditions as herein described.

Foliage:

*Habit.*—Simple, alternate, and borne on semi-rigid petioles 3 to 6 inches in length.

*Size.*—At maturity, the leaves reach 7 to 9 inches from base to apex, and at their widest point the leaves are 6 to 7 inches in width.

*Shape.*—Triangular-cordate with acuminate tip between rounded-based lobes.

*Texture.*—Firm, crisp, but not brittle; sparsely hirtellous on both surfaces.

*Margin.*—Doubly serrate.

*Color.*—Immature: Top surface: RHS 137A with red cast. Under surface: RHS 47B with veins colored RHS 142B. Mature: Top surface: RHS 147A. Under surface: RHS 147B with RHS 47B cast.

*Venation.*—Reticulate.

Flower:

*Habit.*—Flowering is presented on a pendulous raceme. Often, but not always, secondary male and female flowers will develop below the primary male and female flowers. Some peduncles have a solitary male flower, while others may have a solitary male flower accompanied by either a solitary secondary male flower or matching female flower and occasionally a secondary male and female flower.

*Natural flowering season.*—Summer and fall months.

*Lastingness of the individual bloom.*—It takes approximately 5–6 weeks for pollinated female flowers to ripen; individual blooms fade and the petals wither.

*Size.*—Male: Approximately 3.5 to 5 inches by 3 to 3.5 inches (not round). Female: Approximately 2.5 to 3 inches.

*Buds.*—Flat, nearly round, tending towards bell shaped. Just before the buds opens, it is about 4 cm long and about 4.5 cm wide. Bud color is red, RHS 49A.

*Borne.*—On small pedicels originating from long (5 to 8 inches) axillary peduncles, resulting in a solitary male flower, a solitary male and one or two female flowers, and occasionally secondary male and female flowers as raceme develops.

*Peduncle.*—Red, RHS 45 A, on the top surface where exposed to direct light, and about RHS 154 D with a light cast of RHS 42 A where exposed to indirect light.

*Quantity.*—Approximately 2 to 5 flowers per peduncle and numerous (3 to 5) peduncles per shoot, with 5 to 7 shoots per plant.

Sepals:

*Number of sepals.*—2.

*Size of sepals.*—4–4.5 cm long, 6.5–7 cm wide.

*Shape of sepals.*—Orbicular, with slightly dentate margins.

Tepals:

*Shape.*—Round to obovate.

*Color.*—Top surface: In spring and summer when opening, whitish pink RHS 56 D, blushing to RHS 56B to 56C pink, yellow-orange RHS 14B at attachment. Under surface: RHS 56A and 56B in blotches with white. Sepal back can be as dark as RHS 41B.

*Number.*—Approximately 65 to 70 on male flowers and 5 on female flowers.

*Size.*—Outer (male) up to 2.0 inches by 1.5 inches, sometimes greater in width than length.

Reproductive organs:

*Stamens.*—Fully petaloid.

*Pistils.*—Stigma shape: Multi-lobed. Stigma color: RHS 17B. Style color: RHS 17A. Ovaries: Number: 3. Size: Approximately ⅝–¾ inches. Color: RHS 144C with RHS 41A on tips if grown in high light.

Seeds/fruit: None observed to date.

Resistance to disease: Good resistance to powdery mildew, other fungus, and to Xanthomonas bacteria blight.

I claim:

1. A new and distinct cultivar of Begonia plant named '77KK Blush Pink', as illustrated and described.

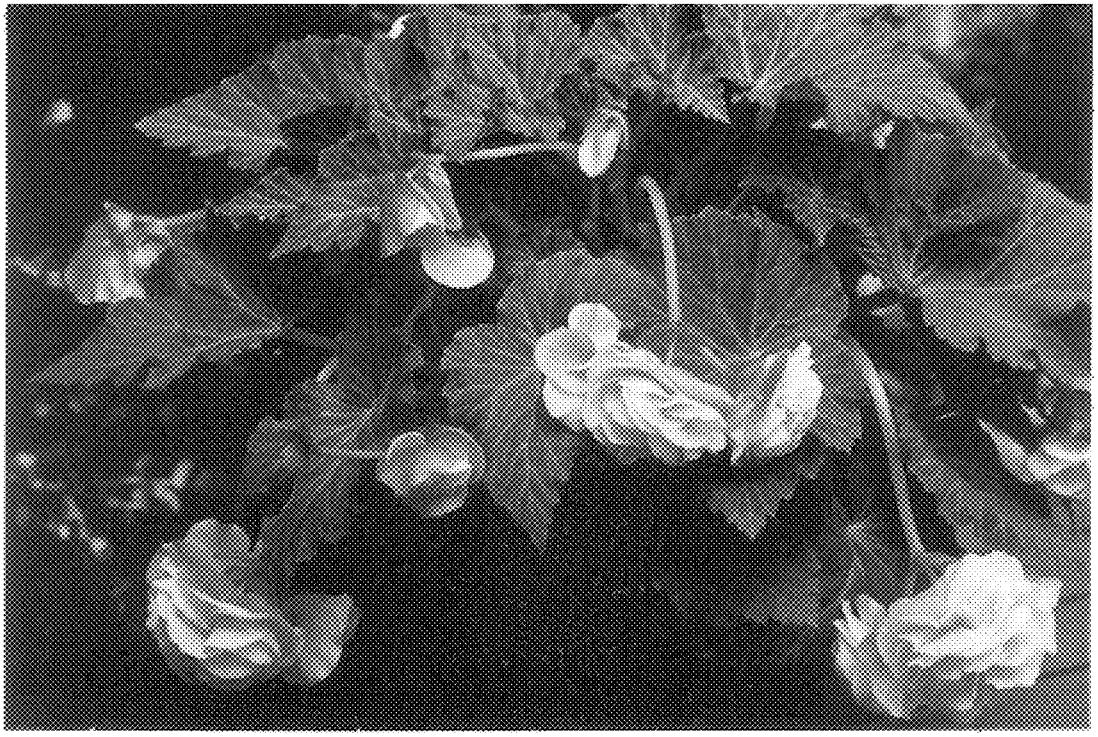

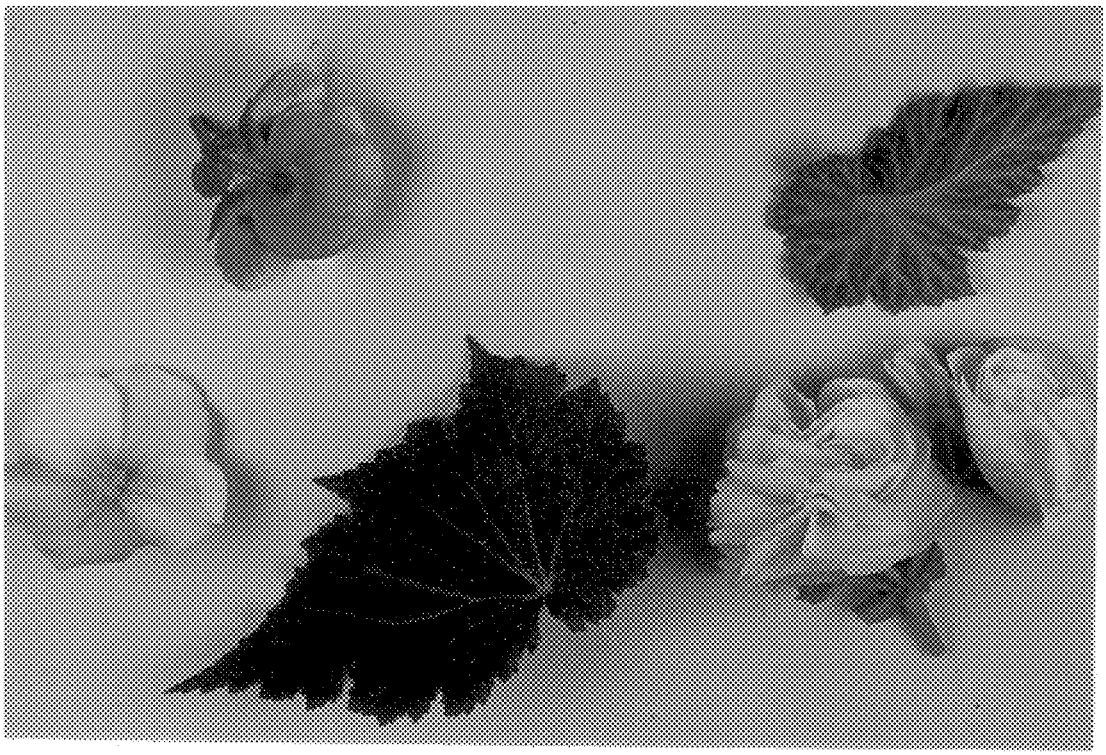

* * * * *